United States Patent
Sumner

(10) Patent No.: US 12,138,259 B1
(45) Date of Patent: *Nov. 12, 2024

(54) METHOD OF CONTROLLING DEPRESSION IN SUBJECTS TREATED FOR OPIOID DEPENDENCE

(71) Applicant: OREXO AB, Uppsala (SE)

(72) Inventor: Michael John Sumner, Malvern, PA (US)

(73) Assignee: OREXO AB, Uppsala (SE)

( * ) Notice: Subject to any disclaimer, the term of this patent is extended or adjusted under 35 U.S.C. 154(b) by 18 days.

This patent is subject to a terminal disclaimer.

(21) Appl. No.: 18/194,678

(22) Filed: Apr. 3, 2023

Related U.S. Application Data

(63) Continuation of application No. 17/363,877, filed on Jun. 30, 2021, now Pat. No. 11,617,746.

(60) Provisional application No. 63/046,258, filed on Jun. 30, 2020.

(51) Int. Cl.
  *A61K 31/485* (2006.01)
  *A61K 9/00* (2006.01)
  *A61P 25/24* (2006.01)
  *A61P 25/36* (2006.01)

(52) U.S. Cl.
  CPC ............ *A61K 31/485* (2013.01); *A61K 9/006* (2013.01); *A61P 25/24* (2018.01); *A61P 25/36* (2018.01)

(58) Field of Classification Search
  CPC .............................. A61K 31/485; A61P 25/36
  USPC .................................................. 514/279, 282
  See application file for complete search history.

(56) References Cited

U.S. PATENT DOCUMENTS

| | | | |
|---|---|---|---|
| 10,986,071 | B2 | 4/2021 | McFarland et al. |
| 11,617,746 | B1 * | 4/2023 | Sumner ................ A61K 31/485 514/282 |
| 11,986,472 | B1 | 5/2024 | Sumner |
| 2012/0178771 | A1 | 7/2012 | Babul et al. |
| 2020/0187777 | A1 | 6/2020 | Luderer et al. |
| 2021/0226930 | A1 | 7/2021 | McFarland et al. |
| 2022/0139554 | A1 | 5/2022 | Pillay et al. |

FOREIGN PATENT DOCUMENTS

| | | |
|---|---|---|
| WO | 2017139761 A1 | 8/2017 |

OTHER PUBLICATIONS

Beck et al., Cognitive Therapy of Substance Abuse, 1993.
Beevers et al., "Effectiveness of an Internet Intervention (Deprexis) for Depression in a United States Adult Sample: A Parallel-Group Pragmatic Randomized Controlled Trial," J Consult Clin Psychol 2017, vol. 85, No. 4, pp. 367-380.
Diclemente et al., "Motivation for Change and Alcoholism Treatment," Alcohol Research & Health 1999;23(2):pp. 86-92.
D'Zurilla et al., "Problem-Solving Therapy," Handbook of Cognitive-Behavioral Therapies, 2010, Ch.7, pp. 197-225.
Kadden et al., "Cognitive-Behavioral Coping Skills Therapy Manual: A Clinical Research Guide for Therapists Treating Individuals with Alcohol Abuse and Dependence," NIAAA Project MATCH Monograph Series vol. 3 1992, (Reprint 2003).
Noar et al., "Rethinking Positive and Negative Aspects of Alcohol Use: Suggestions from a Comparison of Alcohol Expectancies and Decisional Balance," Journal of Studies on Alcohol, Jan. 2003; 64(1):pp. 60-69.
Nyamathi et al., "Effect of Motivational Interviewing on Reduction of Alcohol Use," Drug Alcohol Depend. Feb. 1, 2010; 107(1):pp. 23-30.
Sitharthan et al., "Cue Exposure in Moderation Drinking: A Comparison with Cognitive-Behavior Therapy," J Consult Clin Psychol., Oct. 1997;65(5):pp. 878-882.
Vest et al., "Parallel Modeling of Pain and Depression in Prediction of Relapse During Buprenorphine and Naloxone Treatment: A Finite Mixture Model," Drug and Alcohol Dependence, vol. 209, 2020, 107940, pp. 1-8.
Zill et al., "Vorvida: Study Protocol of a Randomized Controlled Trial Testing the Effectiveness of Internet-Based Self-Help Program for the Reduction of Alcohol Consumption for Adults," BMC Psychiatry 2016;16:19, pp. 1-9.
Zill et al., "The Effectiveness of an Internet Intervention Aimed at Reducing Alcohol Consumption in Adults: Results of a Randomized Controlled Trial (VORVIDA)," Dtsch Arztebl Int 2019; 116:pp. 127-133.
Wong et al., "Comparing rapid micro-induction and standard induction of buprenorphine/naloxone for treatment of opioid use disorder: protocol for an open-label, parallel-group, superiority, randomized controlled trial," Addiction Science & Clinical Practice, 2021, 16:11, pp. 1-10.

* cited by examiner

*Primary Examiner* — Charanjit Aulakh
(74) *Attorney, Agent, or Firm* — DLA PIPER LLP (US)

(57) ABSTRACT

The present disclosure is directed to a method of combatting opioid dependence in a subject experiencing a depressive episode. The method comprises treating the subject with an opioid agonist whilst managing their depression or depressive disorder using a step-wise interactive process, particularly where the process involves virtual cognitive behavioral therapy comprising a program for self-treatment. The self-treatment program could be embodied as a mobile medical application.

22 Claims, 2 Drawing Sheets

METHOD OF CONTROLLING DEPRESSION IN SUBJECTS TREATED FOR OPIOID DEPENDENCE

CROSS-REFERENCE TO RELATED APPLICATIONS

The present application is a continuation of U.S. patent application Ser. No. 17/363,877, titled METHOD OF CONTROLLING DEPRESSION IN SUBJECTS TREATED FOR OPIOID DEPENDENCE, filed Jun. 30, 2021, which claims priority to U.S. Provisional Application No. 63/046,258, titled A METHOD OF CONTROLLING DEPRESSION IN SUBJECTS TREATED FOR OPIOID DEPENDENCE, filed Jun. 30, 2020, each of which is hereby incorporated by reference herein in its entirety.

BACKGROUND

Long-term opioid therapy (LOT) is known to promote incident, recurrent and treatment-resistant major depression. Depression in subjects misusing opioids also frequently complicates the management of opioid dependence. For example, the use of anti-depressants to treat depression in subjects on an opioid agonist therapy (OAT) program can lead to increased program drop outs due to adverse events. A need therefore exists for convenient and effective methodologies to treat opioid dependence in depressed subjects.

SUMMARY

Superior clinical outcomes, such as but not limited to superior efficacy, safety and/or patient compliance are expected in combatting opioid dependence in subjects who are depressed, by opioid agonist treatment (OAT) with concomitant management of depression using cognitive behavioral therapy (CBT). The CBT may be conducted by, or with the assistance of, a physician or therapist, and may preferably be self-directed, and comprises, in particular, the interaction of the OAT participant with an online-based program, which can be accessed via computer, a laptop, a mobile phone or a tablet PC using an up-to-date browser (Google Chrome, Mozilla Firefox, Internet Explorer or Safari). The physician/therapist led CBT or, more particularly, the self-directed, online-based CBT comprises one or more of the following evaluation exercises (e.g., modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

Thus, in one aspect, the present disclosure provides a method of treating opioid dependence in a patient experiencing a depressive episode or with a history of depression, wherein the patient is administered opioid agonist treatment (OAT) and concomitantly the depression or depressive disorder is managed using cognitive behavioral therapy (CBT).

In one embodiment, the subject is administered a combination of buprenorphine and naloxone.

In one embodiment, the subject is administered a combination of buprenorphine and naloxone given sublingually.

In one embodiment, the subject is administered buprenorphine.

In one particular aspect, the present disclosure provides a method of treating opioid dependence in a patient experiencing a depressive episode or with a history of depression, wherein the patient is administered a sublingual dose of buprenorphine and naloxone to the patient effective to manage the patient's withdrawal symptoms and cravings; and concomitantly the depression or depressive disorder is managed using cognitive behavioral therapy (CBT).

In one embodiment, the opioid agonist is administered to the subject for the maintenance treatment of opioid dependence.

In one embodiment, a combination of buprenorphine and naloxone is administered sublingually to the subject for the maintenance treatment of opioid dependence.

In one embodiment, SUBOXONE® is administered to the subject for the maintenance treatment of opioid dependence.

In one embodiment, ZUBSOLV® is administered to the subject for the maintenance treatment of opioid dependence.

In one embodiment, cognitive behavioral therapy (CBT) involves the self-directed management of depression or a depressive disorder by the patient aided by interaction with a CBT program that helps manage the depressive episode.

As used herein, "self-directed management" means the patient directly interacts with a program that addresses aspects of depression, rather than conversing about the patient's depression with a physician or therapist.

Thus, a particular embodiment of the present disclosure provides a method of treating opioid dependence in a patient experiencing a depressive episode or with a history of depression, comprising:
  a. administering a sublingual dose of buprenorphine and naloxone to the patient effective to manage the patient's withdrawal symptoms and cravings; and
  b. self-directed management of depression or a depressive disorder by the patient aided by interaction with a program that helps manage the depressive episode using cognitive behavioral therapy (CBT).

In one embodiment, the patient is suffering from chronic depression.

In one embodiment, the patient is suffering from recurrent depression.

In one embodiment, the patient is suffering from mild-to-moderate depression.

In one embodiment, management of depression or a depressive disorder in subjects administered OAT is achieved using virtual CBT.

In one embodiment virtual CBT is given via an interactive online-based program, which can be accessed via computer, a laptop, a mobile phone or a tablet PC using an up-to-date browser (Google Chrome, Mozilla Firefox, Internet Explorer or Safari).

In one embodiment, the interactive online-based program includes of one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

In one embodiment, the interactive online-based program content is adjusted based on input from the patient. In a particular embodiment, the content is adjusted using artificial intelligence to analyze input from the patient.

In a preferred embodiment, the interactive online-based program is the web-based software platform product DEPREXIS®.

In a particular embodiment, DEPREXIS® is accessible from a mobile device, such as a laptop computer, a tablet or a smartphone.

In a particular embodiment, DEPREXIS® is accessible from a wearable device. The wearable device may also be used to drive further content for, and patient interaction with, the program.

FIGURES

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
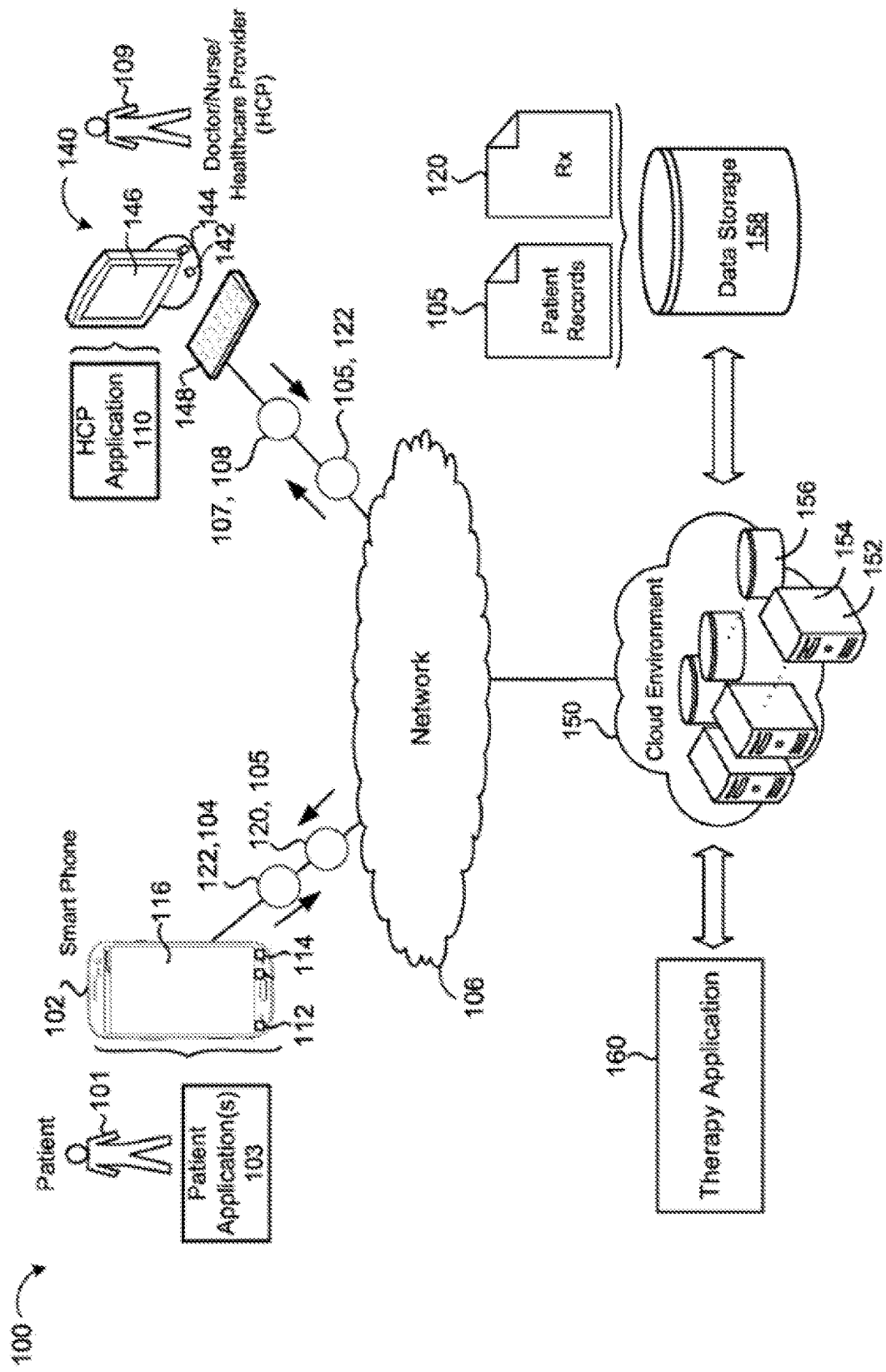
FIG. 1 is a diagram of a digital therapeutic system, in accordance with an embodiment of the present disclosure.

This disclosure is not limited to the particular systems, devices and methods described, as these may vary. The terminology used in the description is for the purpose of describing the particular versions or embodiments only, and is not intended to limit the scope of the disclosure.

Definitions

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "pharmaceutical" is a reference to one or more pharmaceuticals and equivalents thereof known to those skilled in the art, and so forth.

As used herein, the term "about" means plus or minus 10% of the numerical value of the number with which it is being used. Therefore, about 1 mg means in the range of 0.9 mg to 1.1 mg.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by injection, topical administration, oral administration, buccal administration, sublingual administration, transdermal administration, or by any of these methods in combination with other known techniques. "Administering" can include administration by any individual, including, for example, self-administration or administration by a healthcare professional.

"Engaging" when in used in conjunction with a digital therapeutic system, a cognitive behavioral therapy program, or other systems/programs that provide therapy content to patients means to directly or indirectly interact and/or receive treatment or therapy from the system or program based on the provided therapy content. "Engaging" with such a system or program can be accomplished by reading therapy content, responding to therapy content (e.g., filling out questionnaires or answering questions), participating in a conversation with the therapy content (e.g., reading and answering material meant to simulate a conversational flow), and/or otherwise interacting with the provided therapy content. "Engaging" can include a user engaging with the therapy content or the user being instructed to engage with the content (e.g., by a healthcare provider (HCP)).

A "therapeutically effective amount" or "effective amount" of a composition is a predetermined amount calculated to achieve the desired effect, i.e., to case, inhibit, block, or reverse a disorder. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range. The compounds may be delivered once daily, once weekly, multiple times daily, or multiple times weekly. However, it will be understood that the effective amount administered will be determined by the physician in the light of the relevant circumstances including the condition to be treated, the choice of compound to be administered, and the chosen route of administration, and therefore the above dosage ranges are not intended to limit the scope of embodiments herein in any way. A therapeutically effective amount of compound of this invention is typically an amount such that when it is administered in a physiologically tolerable excipient composition, it is sufficient to achieve an effective systemic concentration or local concentration in the tissue.

Controlling Depression in Subjects Treated for Opioid Dependence

Described herein and various techniques, systems, and/or compositions for controlling or assisting individuals in controlling depression, particularly for individuals being treated for opioid dependence. In some embodiments, the aforementioned techniques and/or systems can utilize CBT. CBT is a psychotherapeutic approach that influences dysfunctional emotions, behaviors and cognitions using goal-oriented, systematic procedures. CBT includes a number of psychological techniques that share a theoretical basis in behavior learning theory and cognitive psychology. The present principles are directed to CBT, particularly virtual CBT comprising a program for self-treatment, enabling a user with the means to self-manage depression or a depressive disorder. The user of the program, according to the present disclosure, is concomitantly treated for opioid dependence with an opioid agonist.

Thus, the present disclosure provides, in one aspect, a method of treating opioid dependence in a patient experiencing a depressive episode or with a history of depression, wherein the patient is administered opioid agonist treatment (OAT) and concomitantly the depression or depressive disorder is managed using cognitive behavioral therapy (CBT).

Suitable opioid agonists include, for example, a full opioid agonist such as methadone or a partial opioid agonist such as buprenorphine. The buprenorphine may be given alone or in combination with the opioid receptor antagonist naloxone. Conveniently, the combined buprenorphine-naloxone product is administered sublingually. Examples of suitable sublingual buprenorphine-naloxone products include SUBOXONE® and ZUBSOLV®. Alternatively, buprenorphine or buprenorphine/naloxone may be administered by intramuscular injection. Buprenorphine or buprenorphine/naloxone may also be administered by subcutaneous injection.

In one particular aspect, the present disclosure provides a method of treating opioid dependence, e.g. maintenance treatment of opioid dependence in a patient, wherein the patient is concurrently experiencing a depressive episode or with a history of depression, comprising:
 a. administering a sublingual dose of buprenorphine and naloxone to the patient effective to manage the patient's withdrawal symptoms and cravings; and
 b. managing the depression or depressive disorder using personalized, virtual CBT, by completing one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

The methods described herein are generally applicable to recipients of opioid agonist treatment (OAT) with depression or a depressive disorder who are currently experiencing a depressive episode. The management of depression or a depressive disorder in these subjects is achieved using cognitive behavioral therapy (CBT), for example personalized virtual CBT given via an interactive online-based program, accessible using, for example, a computer, a laptop, a mobile phone or a tablet PC and an up-to-date browser (e.g. Google Chrome, Mozilla Firefox, Internet Explorer or Safari). The program may also be incorporated into an application ("an app") accessible from a mobile phone or wearable device, which may also be used to drive further content for, and patient interaction with, the program.

The interactive online-based program comprising one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions. In one embodiment, the interactive online-based program comprising all ten modules (i) to (x).

Following an introduction to the program's function and purpose, the evaluation exercises/modules are completed. The order in which the modules are presented varies depending on users' expressed interests and current concerns. Within each module, users can continuously choose among different response options and thereby alter the specific path and subsequent content. For example, each module offers briefer versus more elaborated versions of the same content, which can be selected based on personal preferences.

Each exercise/module is further described as follows:

(i) Psychoeducational: an overview of the CBT model of depression (e.g., relationships among thoughts, behaviors, and feelings); exploring perceived reasons for depression; brief mindfulness exercise: learning to calmly observe the flow of thoughts and feelings; worksheet to encourage regular program use; prompting to complete mood questionnaires.

(ii) Behavioral activation: learning about the relationship between activities and depression; explaining the concept of basic psychological needs, which may or may not be satisfied by certain activities (e.g., competence, autonomy, relatedness); brief audio recordings on each need; exploring lists of activity suggestions and choosing suitable activities; discussion of how obstacles in activity pursuit might be overcome (e.g., lack of motivation).

(iii) Cognitive modification: learning about triggers and consequences of automatic thoughts (ATs) and selected cognitive distortions (e.g., catastrophizing, emotional reasoning); identifying and coping with unhelpful ATs in daily life; using mental imagery to challenge and refute illogical ATs (the "scientist perspective") or to mentally detach oneself from unhelpful ATs (the "bird's eye" and "wise old man" perspective).

(iv) Mindfulness and acceptance: learning about and experiencing the effects of thought suppression and emotional control efforts (e.g., exercise: "Don't think of a pink elephant for one minute"); learning about willingness to experience unpleasant thoughts and feelings as an alternative to control-oriented strategies; exercises to practice mindfulness and acceptance (e.g., mental imagery: imagining thoughts drifting away on a stream); clarifying personal values and building commitment to pursue value-consistent goals even in the presence of distressing thoughts or feelings.

(v) Interpersonal skills: learning about the relationship between interpersonal behavior/functioning and depression; practicing potentially helpful communication styles (e.g., assertive behavior, modulating posture and voice and observing effects on mood); modulating behavior in relationship contexts and observing effects on mood (e.g., non-blaming communication; responding enthusiastically rather than cynically to good news).

(vi) Relaxation, physical exercise and lifestyle modification: learning about different relaxation exercises to cope with stress and reduce tension; diaphragmatic breathing and mental imagery exercises ("beach, country road, and sunset imagery"); muscle relaxation exercise; exploration of lifestyle habits that can facilitate well-being (healthy nutrition, regular exercise, sleep hygiene).

(vii) Problem-solving: learning about a structured approach to problem-solving; defining problems in concrete, specific rather than vague terms; setting achievable goals; generating and evaluating potential problem-solution plans; implementing problem solving plans and evaluating their impact; practicing problem-solving with example situations.

(viii) Childhood experiences: learning about early learning experiences and later vulnerability to depression (e.g., formation of certain beliefs or schemas as a consequence of early learning experiences); dealing with distressing memories with the technique of therapeutic writing; learning about forgiveness as a potentially helpful strategy; exploring the idea of creating new, positive memories by focusing on current and future learning experiences.
 (ix) Positive psychology: learning about selected core principles of positive psychology (focusing on strengths and talents rather than problems or deficits); exploring different strategies to foster well-being and happiness (e.g., savoring positive experiences, satisfying basic psychological needs, discovering and cultivating personal talents and strengths).
 (x) Dream work and emotion focused interventions: (generally offered only to those who express an interest in this topic) dreams as vehicles for daily problem-solving, coping with distressing dreams (e.g., keeping a dream journal and rewriting dreams with positive endings); learning about other emotion-focused therapeutic methods.

The interactive online-based program provides a remotely managed, fully automated digital therapy, which can be used by the subject without the involvement or guidance of a physician or therapist, although it may be beneficial to have the support of a healthcare provider for certain subject groups. The program can be tailored to individual patients, and is conveniently available 24 hours each day as a 10-week (or 12-week) course of modules. The program content may be adjusted based on input from the patient, e.g. using artificial intelligence to analyze input from the patient. Thus, it can respond individually to patient's or consumer's feedback and adjust the content accordingly.

The interactive online-based program also provides information on depression, presents exercises, methods and techniques, and supports patients and consumers in their implementation. Additionally, the program may offer information via emails or text messages to deal with the contents of the exercise and to integrate them into daily routine.

One particular interactive online-based program which may be used as part of the present disclosure is the web-based software platform product DEPREXIS®. The product DEPREXIS®, together with the further details of DEPREXIS® and its use discussed in https://www.c4tbh.org/program-review/DEPREXIS/, are incorporated by reference herein in their entirety. DEPREXIS® is a web-based software platform, able to be used at any time during the 10-week (or 12-week) program on any device with a compatible browser. DEPREXIS® is accessed with an individual user key and personal user ID to ensure that the user experience is private and confidential. The usage period per access key is 12 weeks after initial registration. DEPREXIS® provides personalized virtual cognitive behavioral therapy for individuals, 18 years or older, with depression or a depressive disorder who are looking to mitigate a depressive episode. DEPREXIS® can be used in conjunction with treatment by a healthcare professional if desired or recommended. DEPREXIS® guides users through the program in a dynamic dialog and no special computer skills are required. DEPREXIS® can be used as a standalone self-help tool, but may also be used in a therapist-guided model of care. The content of DEPREXIS® is delivered in 10 modules [i.e. (i) to (x) hereinabove] that explain and provide examples of CBT techniques, and allow the user to practice them. An introductory module asks for the user's main concerns and preferences, and the modules are presented to the user with content that is tailored to their needs. Users are encouraged to complete all of the modules, although they may experience benefits without completing them all.

Each module explains the context or rationale of each therapeutic element and suggests ways that the user can apply that element to their day-to-day life. For example, the problem-solving module explains several concepts such as defining vague problems in specific terms, generating alternative solutions, choosing one option and checking whether this has helped to solve the problem. Specific examples are given and the user can download a worksheet to try out the skills learned. In each module the user reads information and then selects one of several pre-set responses. The program selects the subsequent material to match this response, in what is described as a 'simulated dialogue' to tailor the content to the user. For example, the users are asked about their perceived reasons for their depression; if the user selects the option that the depression relates to a recent bereavement then this is acknowledged in later modules. The user can also select how much detail they want to read in each module. Each module is expected to take between 10 and 60 minutes to complete, depending on the user's reading speed and what tailored content is presented. It is intended that the user will complete 1 module per week for 10 weeks. The program can be accessed on any device that has internet access. Users log into the program through an encrypted website, using their own login and password. DEPREXIS® is mainly text-based but also includes audio content, photographs and drawings. It also includes worksheets and summary sheets. Users can get daily motivational messages by email.

The opioid agonist may be administered to the subject to treat opioid dependence according to dose regimens well-known in the art, for example as described in drug product labels approved by the US FDA. In one embodiment, buprenorphine and naloxone are administered sublingually for the maintenance treatment of opioid dependence. In a particular embodiment, SUBOXONE® is administered sublingually for the maintenance treatment of opioid dependence. In another particular embodiment, ZUBSOLV® is administered sublingually for the maintenance treatment of opioid dependence. Buprenorphine and naloxone may conveniently be administered as a sublingual film (e.g. SUBOXONE®) at a daily dose of 16 mg buprenorphine: 4 mg naloxone. Buprenorphine and naloxone may conveniently be administered as a sublingual tablet (e.g. ZUBSOLV®) at a daily dose of 11.4 mg buprenorphine: 2.8 mg naloxone. In certain aspects, subjects who are performing well during the evaluation herein, or successfully completed the evaluation, may be candidates for an amended OAT regimen, e.g. a reduction in the daily dose or frequency of dosing of the opioid agonist and/or amendment of the daily dose of any drug medication they have been prescribed to manage depression.

Inaction to treat, or inaction to appropriately treat, depression in individuals receiving OAT for opioid dependence can result in an increased risk for a relapse to opioids or other substances, and may lead to a host of other negative clinical outcomes, including exacerbation of psychiatric comorbidities, such as anxiety, panic, traumatic intrusions, and/or suicidal intent.

Therefore, in one aspect, the present disclosure provides a method of reducing the likelihood of opioid relapse during treatment of opioid dependence, e.g. maintenance treatment of opioid dependence, in a patient with depression, comprising:
 a. administering a sublingual dose of buprenorphine and naloxone to the patient effective to manage the patient's withdrawal symptoms and cravings; and
 b. self-directed management of a depressive episode aided by interaction with a program that includes one or more of the following evaluation exercises (e.g. modules): (i)

psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

In another aspect, the present disclosure provides a method of mitigating psychiatric comorbidities during treatment of opioid dependence, e.g. maintenance treatment of opioid dependence. in a patient with depression, comprising:

a. administering a sublingual dose of buprenorphine and naloxone to the patient effective to manage the patient's withdrawal symptoms and cravings; and b. self-directed management of a depressive episode aided by interaction with a program that includes one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

Referring now to FIG. 1, there is shown a diagram of a digital therapeutic system 100. In various embodiments, the digital therapeutic system 100 can be utilized to implement one, some, or all of the techniques or features described above. In one embodiment, the digital therapeutic system 100 can provide a patient 101 access to a digital therapeutic 120 (e.g., CBT) via a therapy application 160 (e.g., DEPREXIS®) and facilitate or encourage interaction between the patient 101 with the digital therapeutic 120. In one embodiment, the patient 101 can interact with the therapy application 160 via a patient device 102. In this embodiment, the therapy application 160 can be accessed via a patient application 103 stored on the patient device 102, such as a browser (e.g., in a web-based implementation of the therapy application 160) or another software application (e.g., a smartphone app). In another embodiment, the therapy application 160 can be downloaded onto and directly executed by the patient device 102. Further, the digital therapeutic system 100 can monitor inputs or events associated with the patient's 101 interaction with the digital therapeutic 120. In various embodiments, the digital therapeutic 120 could be prescribed to the patient 101 (e.g., by a HCP 109) or be available without a prescription. According to implementations in which the digital therapeutic 120 is not prescribed, the person using or being administered the digital therapeutic may be referred to as a "user." A "user" may include a patient 101 or any other person using or being administered the digital therapeutic 120, irrespective of whether the digital therapeutic 120 was prescribed to that person.

In some embodiments, the digital therapeutic 120 may include or be combined with traditional drug therapy (e.g., buprenorphine-containing products, such as stand-alone buprenorphine, or products including buprenorphine and other drugs such as naloxone, such as ZUBSOLV®), which similarly may or may not require a prescription. An authorized HCP 109 may prescribe the patient 101 the digital therapeutic 120 designed to treat symptoms in the patient 101. The HCP 109 may include a physician, nurse, clinician, or other qualified health professionals. The HCP 109 may provide any suitable level of supervision to the patient 101, including little to no supervision.

In some embodiments, the system 100 can include a network 106, a patient device 102, and a therapy application 160. The network 106 can provide access to cloud computing resources 150 (e.g., a distributed system) that execute the therapy application 160 to provide for the performance of services on remote devices, which can be accessed by the patient 101 via the patient application 103. In some embodiments, the system 100 can further include an HCP system 140, which is described below. In some embodiments, the network 106 allows for interaction between patients 101 and/or HCPs 109 and the therapy application 160. For instance, the therapy application 160 may provide the patient 101 access to the digital therapeutic 120 and receive user input or event data 122 input by the patient 101 associated with the patient's 101 interaction with the digital therapeutic 120. In turn, the therapy application 160 may store the event data 122 on a storage resource 156.

The network 106 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, fifth generation (5G) network, a satellite communications network, and other communication networks. The network 106 may include one or more of a Wide Area Network (WAN), a Local Area Network (LAN), and a Personal Area Network (PAN). In some examples, the network 106 includes a combination of data networks, telecommunication networks, and a combination of data and telecommunication networks. The patient device 102, the HCP system 140, and/or the therapy application 160 communicate with each other by sending and receiving signals (wired or wireless) via the network 106, which, in some examples, may utilize Bluetooth, Wi-Fi, etc. In some examples, the network 106 provides access to cloud computing resources, which may be elastic/on-demand computing and/or storage resources 156 available over the network 106. The term "cloud" services generally refers to a service delivered from one or more remote devices accessible via one or more networks 106, rather than a service performed locally on a user's device.

The patient device 102 may include, but is not limited to, a portable electronic device (e.g., smartphone, cellular phone, personal digital assistant, laptop computer, or wireless tablet device), a desktop computer, or any other electronic device capable of sending and receiving information via the network 106. The patient device 102 includes data processing hardware 112 (a computing device that executes instructions), memory hardware 114, and a display 116 in communication with the data processing hardware 112.

In some embodiments, the patient device 102 can execute the patient application 103 (or accesses a web-based patient application) for establishing a connection with the therapy application 160 to access the digital therapeutic 120. For instance, the patient 101 may have access to the therapy application 160 via the patient application 103 for a duration (e.g., 3 months) of the digital therapeutic 120 prescribed to the patient 101. Here, the patient device 102 may launch the patient application 103 by initially providing an access code 104 when the digital therapeutic 120 is prescribed by the HCP 109, the access code 104 allowing the patient 101 to access content associated with the digital therapeutic 120 from the therapy application 160. The content may be specifically tailored for treating/addressing one or more symptoms associated with the specific indication that the patient 101 may be experiencing. The patient application 103, when executing on the data processing hardware 112 of the patient device 102, is configured to display a variety of graphical user interfaces (GUIs) on the display 116 of the patient device 102 that, among other things, allow the patient 101 to (i) input event data 122 describing one or more parameters associated with the patient 101 (e.g., an indication of how the patient 101 is feeling, an indication of the last time the patient 101 used a drug, an indication of where the patient 101 was located when they last used a drug, an indication of who the patient 101 was with last time they used a drug, an indication of the time of day the patient 101 last used a drug, etc.); (ii) solicit information from the patient 101; (iii) deliver therapeutic content (e.g., CBT content) to the patient 101; (iv) allow the patient 101 to contact their HCP 109; (v) allow the patient 101 to review their progress adhering to their prescription regimen with respect to the digital therapeutic 120 and/or any prescribed medication; (vi) present journal entries for the patient 101 to view and/or edit; and/or (vii) provide questionnaires to the patient 101 or otherwise solicit input or engagement between the patient 101 the provided therapeutic content.

The storage resources 156 may provide data storage 158 for storing the event data 122 received from the patient 101 in a corresponding patient record 105 as well as the digital therapeutic 120 prescribed to the patient 101. The patient record 105 may be encrypted while stored on the data storage 158 so that any information identifying patient 101 is anonymized, but may later be decrypted when the patient 101 or supervising HCP 109 requests the patient record 105 (assuming the requester is authorized/authenticated to access the patient record 105). All data transmitted over the network 106 between the patient device 102 and the cloud computing system 150 may be encrypted and sent over secure communication channels. For instance, the patient application 103 may encrypt the event data 122 before transmitting to the therapy application 160 via the HTTPS protocol and decrypt a patient record 105 received from the therapy application 160. When network connectivity is not available, the patient application 103 may store the event data 122 in an encrypted queue within the memory hardware 114 until network connectivity is available.

In some embodiments, the digital therapeutic system 100 can include an HCP system 140 that is configured to allow a HCP to interact with the patient 101 and/or the therapy application 160. For example, the HCP system 140 could allow the HCP to view a status or information associated with the patient 101 (e.g., information related to whether or when the patient 101 has completed one or more modules associated with the therapy application 160), communicate with the patient 101, and so on. The HCP system 140 may be located at a clinic, doctor's office, or facility administered by the HCP 109 and includes data processing hardware 142, memory hardware 144, and a display 146. The memory hardware 144 and the display 146 are in communication with the data processing hardware 142. For instance, the data processing hardware 142 may reside on a desktop computer or portable electronic device for allowing the HCP 109 to input and retrieve data to and from the therapy application 160. In some examples, the HCP 109 may initially onboard some or all of patient data 107 at the time of prescribing the digital therapeutic 120 to the patient 101. The HCP system 140 includes a keyboard 148, mouse, microphones, speakers and/or a camera.

In some embodiments, the HCP system 140 (i.e., via the data processing hardware 142) executes the HCP application 110 (or accesses a web-based patient application) for establishing a connection with the therapy application 160 to input and retrieve data therefrom. For instance, the HCP system 140 may be able to access the anonymized patient record 105 securely stored by the therapy application 160 on the storage resources 156 by providing an authentication token 108 validating that the HCP 109 is supervising the patient 101 and authorized to access the corresponding patient record 105. The authentication token 108 may identify the particular patient 101 associated with the patient record 105 that the HCP system 140 is permitted to obtain from the therapy application 160. The patient record 105 may include time-stamped event data 122 indicating the patient's interaction with the digital therapeutic 120 through the patient application 103 executing on the patient device 102. The HCP application 110, when executing on the data processing hardware 142 of the HCP system 140, is configured to display a variety of graphical user interfaces (GUIs) on the display 146 of the HCP system 140 that, among other things, allow the HCP 109 to input event data 122 describing one or more parameters associated with the patient 101, solicit information from the patient 101, and input clinical notes associated with the patient 101.

In some implementations, the HCP application 110 is in communication with a single patient application 103 for a single patient 101 and manages data associated with the single patient application 103. In other implementations, the HCP application 110 is in communication with several patient applications 103 associated with several patients 101, and the HCP application 110 may manage and display the data associated with the several patient applications 103 in any suitable manner, e.g., by toggling between different views and/or displaying certain data simultaneously. In other implementations, the HCP application 110 is in communication with multiple patient applications 103 for the same patient 101 and simultaneously manages data associated with the multiple patient applications 103. In this implementation, the data from multiple patient applications 103 may be displayed simultaneously in any suitable manner or the data from each patient application 103 may be displayed discretely such that the HCP 109 is able to toggle between the discretely displayed data.

The cloud computing resources 150 may be a distributed system (e.g., a remote environment) having scalable/elastic resources 152. The resources 152 include computing resources 154 (e.g., data processing hardware) and/or the storage resources 156 (e.g., memory hardware). The cloud computing resources 150 execute the therapy application 160 for facilitating communications with the patient device 102 and the HCP system 140 and storing data on the storage resources 156 within the data storage 158. In some examples, the therapy application 160 and the data storage 158 reside on a standalone computing device. The therapy application 160 may provide the patient 101 with the patient application 103 (e.g., a mobile application, a web-site application, or a downloadable program that includes a set of instructions) executable on the data processing hardware 112 and accessible through the network 106 via the patient device 102 when the patient 101 provides a valid access code 104. Similarly, the therapy application 160 may provide the HCP 109 with the HCP application 110 (e.g., a mobile application, a web-site application, or a downloadable program that includes a set of instructions) executable on the data processing hardware 142 and accessible through the network 106 via the HCP system 140.

In one embodiment, the therapy application 160 can include an interactive program that presents information or other resources to the patient 101 and receive input or feedback from the patient 101. The therapy application 160 can implement or utilize CBT techniques, for example. In one embodiment, the therapy application 160 can include a variety of different modules that the patient 101 interacts with. In one embodiment, the modules can include a psycho-education module, a behavioral activation module, a cognitive modification module, a mindfulness and acceptance module, an interpersonal skills module, a relaxation module, a physical exercise and lifestyle modification module, a problem solving module, an expressive writing and forgiveness or childhood experiences module, a positive psychological interventions module, and/or a dream work and emotion-focused interventions module. Each of the modules can present information/resources to the patient 101 in a manner consistent with CBT techniques and/or in a manner that allows the patient 101 to implement CBT techniques for self-directed therapy. Various descriptions of illustrative embodiments of the aforementioned module types are provided above.

As described in greater detail below, for patients 101 suffering from particular conditions (e.g., OUD), providing CBT to the patients 101 (e.g., via the digital therapeutic system 100) in connection with a medication regimen (e.g., an OAT, such as one or more sublingual doses of buprenorphine and naloxone) can assist the patients 101 in managing the comorbidities (e.g., depression, as exhibited by the patients 101 as anxiety, panic, traumatic intrusions, or suicidal intent) associated with their condition better than simply taking the medication regimen alone. Further, assisting patients in managing their depression associated with their condition in turn reduces the risk of relapse and treatment non-compliance, improves patient health, reduces the potential for negative interactions between drugs taken by the patients 101 to address their depression (e.g., benzodiazepines) and the OAT (for example, the buprenorphine in a buprenorphine and naloxone fixed dose combination), and generally improves patient outcomes associated with the medication regimen, which can be referred to as the "safety profile" of the OAT for the patients 101. The digital therapeutic system 100 is particularly advantageous for providing CBT to such patients 101 because the CBT provided thereby is immediately accessible at any time (e.g., via the patient device 102). For patients 101 suffering from depression and other such conditions, having immediate, frictionless access to CBT in this manner can greatly assist them in managing anxiety, panic, traumatic intrusions, and/or suicidal intent and other comorbidities associated with their condition, which in turn improve the effectiveness of their treatment regimen.

Figure 2:
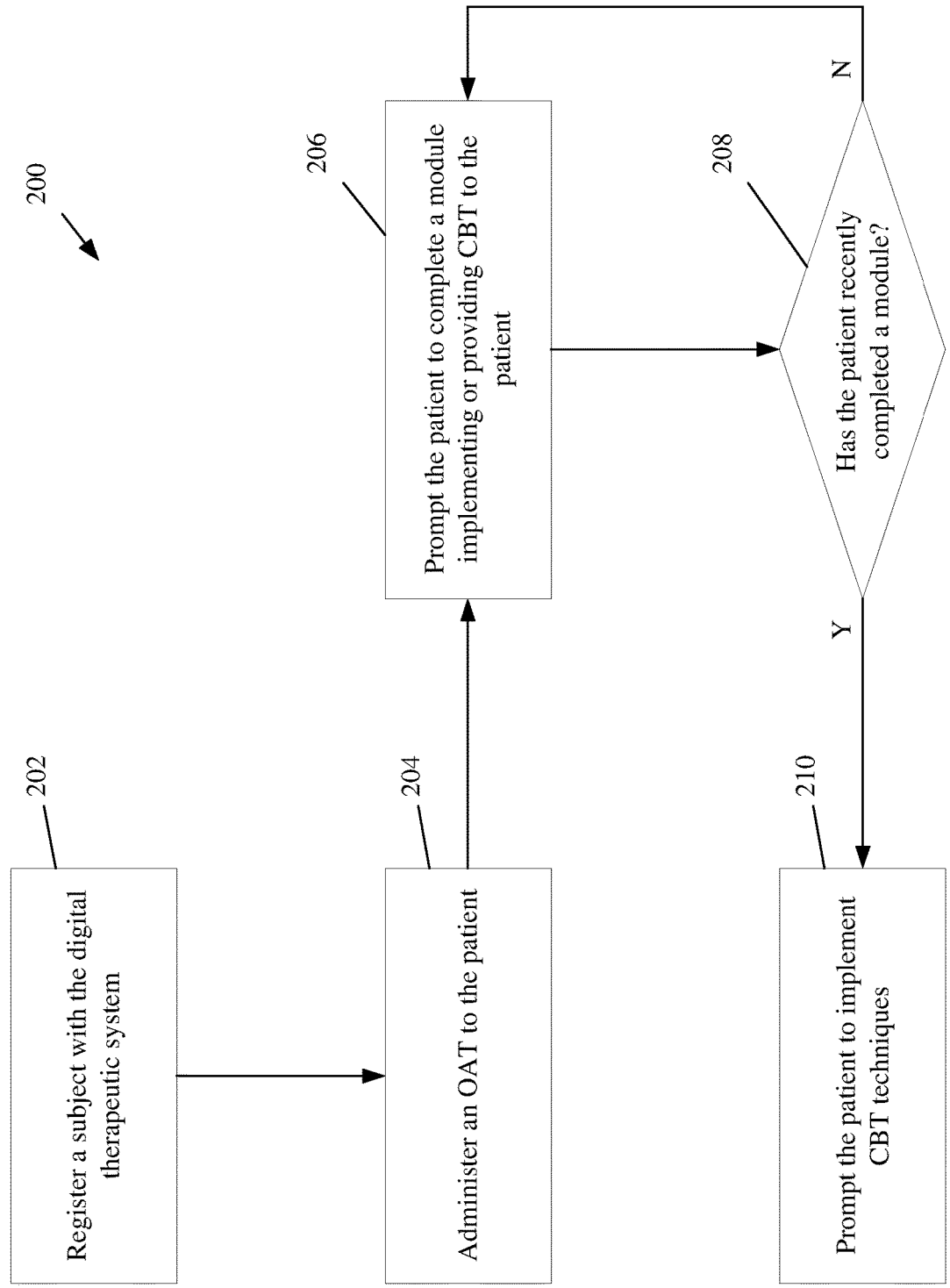
FIG. 2 is a flow diagram of a process using the digital therapeutic system, in according with an embodiment of the present disclosure.

Referring now to FIG. 2, there is shown a process 200 for treating a patient suffering from depression. In one embodiment, the illustrated process 200 can utilize the digital therapeutic system 100 shown in FIG. 1 and described above in connection with an OAT. The process 200 can include registering 202 the patient with the digital therapeutic system 202. In one embodiment, the patient can be registered or otherwise gain access to the digital therapeutic system 100 via an access key, which patients can be required to enter during product registration. In various embodiments, the access to the digital therapeutic system 100 can be time-limited (e.g., 180 days) or indefinite. In some embodiments, the access key can be provided via the HCP in connection with a prescription for the digital therapeutic system 100.

The process 200 can further include administering 204 an OAT to the patient. In one embodiment, the OAT could include a regimen of buprenorphine and naloxone (e.g., ZUBSOLV®). The OAT could be delivered one or multiple times over a variety of different time periods (e.g., once daily, once weekly, multiple times daily, or multiple times weekly). The OAT could also include a variety of different dosages. In one embodiment, the dosages could include from about 0.7 mg to about 17.2 mg of buprenorphine and from about 0.18 mg to about 4.2 mg of naloxone. For example, the dosages could include 0.7 mg buprenorphine/0.18 mg naloxone, 1.4 mg buprenorphine/0.36 mg naloxone, 2.9 mg buprenorphine/0.71 mg naloxone, 5.7 mg buprenorphine/1.4 mg naloxone, 8.6 mg buprenorphine/2.1 mg naloxone, or 11.4 mg buprenorphine/2.9 mg naloxone. The process 200 can further include prompting 206, by the digital therapeutic system 100, the patient to complete a module that implements CBT techniques or otherwise provides CBT to the patient. In some embodiments, the module could be programmed to simulate a dialogue with the patient using, for example, natural language processing or other artificial intelligence systems or techniques. In some embodiments, the module can be programmed to implement various psychotherapeutic approaches. Accordingly, the digital therapeutic system 100 can provide the patient with CBT in conjunction with the administration 204 of the OAT. In various embodiments, the digital therapeutic system 100 can be configured to prompt 206 the patient to complete or view a module by sending a communication (e.g., an email, text message, or push notification) to the patient device 102 associated with the patient 101.

In one embodiment, the digital therapeutic system 100 can be configured to monitor the patient and encourage the patient to interact with the digital therapeutic system 100. In one embodiment of the process 200, the digital therapeutic system 100 can be programmed to determine 208 whether the patient has recently completed or viewed a module. If the patient has not recently completed a module, the digital therapeutic system 100 can prompt 206 the patient to complete a module, which could include the same module that was previously viewed or a new module. Conversely, if the patient has recently completed a module, the digital therapeutic system 100 can prompt 210 the patient to implement the CBT techniques learned from the modules. In one embodiment, the digital therapeutic system 100 can be configured to track when and if the patient has completed all of the modules associated with the therapy application 160.

In the above description of the process 200, it should be understood that the particular order of the steps is simply provided for illustrative purposes and the steps can alternatively occur or be implemented in different orders of operation or could occur contemporaneously with each other, unless explicitly described otherwise. For example, the patient could be registered 202 with the digital therapeutic system 100 after or contemporaneously with being administered 204 the OAT. As another example, the patient could be administered 204 the OAT after or contemporaneously with being prompted 206 to complete a module. The present disclosure is intended to cover all such modifications and different orders of operation of the illustrated process 200.

Accordingly, patients undergoing an OAT regimen can utilize the digital therapeutic system 100 to access the therapy application 160 to receive CBT designed to treat the comorbidities (e.g., depression) associated with their conditions (e.g., opioid dependence) during the course of or otherwise in connection with their treatment regimen. The digital therapeutic system 100 can be configured to provide access to the therapy application 160 via a web-based software program, an app accessible via their smartphone, and so on. Having ready, 24/7, immediate access to CBT provided via the digital therapeutic system 100 greatly improves patient outcomes by helping patients to mitigate the comorbidities associated with their condition, which in turn improves compliance with the treatment regimen, improves their health, and reduces the risk of relapse, among other benefits. Further, treating the comorbidities associated with the condition can correspondingly result in treatment in the condition itself through, e.g., increased compliance of by the patient with the treatment regimen. For example, treatment of the patient's opioid use can be embodied as a decrease in an amount of opioid use by the patient, a decrease in a frequency of the opioid use by the patient, an increase in a number of number of days between instances of the opioid use by the patient, an increase pain tolerance exhibited by the patient before the opioid use, and so on.

SPECIFIC EMBODIMENTS

Embodiment 1: A method of treating opioid dependence in a patient experiencing a depressive episode or with a history of depression, wherein the patient is administered opioid agonist treatment (OAT) and concomitantly the depression or depressive disorder is managed using cognitive behavioral therapy (CBT).

Embodiment 2: The method of Embodiment 1, wherein CBT involves the self-directed management of depression or a depressive disorder by the patient aided by interaction with a CBT program that helps manage the depressive episode.

Embodiment 3: The method of Embodiment 1 or 2, wherein OAT comprises administering a combination of buprenorphine and naloxone.

Embodiment 4: The method of Embodiment 1 or 2, wherein OAT comprises administering sublingually a combination of buprenorphine and naloxone.

Embodiment 5: A method of treating opioid dependence in a patient experiencing a depressive episode or with a history of depression, comprising:
  a. administering a sublingual dose of buprenorphine and naloxone to the patient effective to manage the patient's withdrawal symptoms and cravings; and
  b. self-directed management of depression or a depressive disorder by the patient aided by interaction with a CBT program that includes of one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

Embodiment 6: A method of reducing the likelihood of opioid relapse during treatment of opioid dependence, e.g. maintenance treatment of opioid dependence, in a patient experiencing a depressive episode or with a history of depression, comprising:
  a. administering a sublingual dose of buprenorphine and naloxone to the patient effective to manage the patient's withdrawal symptoms and cravings; and
  b. self-directed management of depression or a depressive disorder by the patient aided by interaction with a CBT program that includes of one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

Embodiment 7: A method of mitigating psychiatric comorbidities during treatment of opioid dependence, e.g. maintenance treatment of opioid dependence, in a patient experiencing a depressive episode or with a history of depression, comprising:
  a. administering a sublingual dose of buprenorphine and naloxone to the patient effective to manage the patient's withdrawal symptoms and cravings; and
  b. self-directed management of depression or a depressive disorder by the patient aided by interaction with a CBT program that includes of one or more of the following evaluation exercises (e.g. modules): (i) psychoeducation; (ii) behavioral activation; (iii) cognitive modification; (iv) mindfulness and acceptance; (v) interpersonal skills; (vi) relaxation, physical exercise and lifestyle modification; (vii) problem solving; (viii) expressive writing and forgiveness or childhood experiences; (ix) positive psychological interventions; (x) dream work and emotion-focused interventions.

Embodiment 8: The method of Embodiment 7, wherein the psychiatric comorbidity is suicidal intent.

Embodiment 9: A method of treating opioid dependence in a patient with depression, the method comprising: administering a sublingual dose of buprenorphine and naloxone to the patient effective to manage the patient's withdrawal symptoms and cravings; and in conjunction with the administration of the sublingual dose of buprenorphine and naloxone, engaging in a self-directed digital, interactive cognitive behavioral therapy program that treats the depression, wherein the depression is treated, thereby treating the opioid dependence.

Embodiment 10: A method of treating opioid dependence with a decreased risk of an adverse reaction or a drug interaction in a patient with depression, the method comprising: administering a sublingual dose of buprenorphine and naloxone to the patient effective to manage the patient's withdrawal symptoms and cravings for an opioid; and in conjunction with the administration of the sublingual dose of buprenorphine and naloxone, engaging in a self-directed digital, interactive cognitive behavioral therapy program that treats the depression, wherein the patient avoids concomitant use of a benzodiazepine, thereby decreasing the risk of the adverse reaction or the drug interaction between the benzodiazepine and the sublingual dose of buprenorphine and naloxone, and thereby improving a safety profile of the sublingual dose of buprenorphine and naloxone administered to the patient.

Embodiment 11: A method of treating opioid dependence with a decreased risk of an adverse reaction or a drug interaction in a patient with depression, the method comprising: administering a sublingual dose of buprenorphine and naloxone to the patient effective to manage the patient's withdrawal symptoms and cravings for an opioid; and in conjunction with the administration of the sublingual dose of buprenorphine and naloxone, engaging in a self-directed digital, interactive cognitive behavioral therapy program that treats depression, wherein the patient decreases concomitant use of a benzodiazepine, thereby decreasing the risk of the adverse reaction or the drug interaction between the benzodiazepine and the sublingual dose of buprenorphine and naloxone, and thereby improving a safety profile of the sublingual dose of buprenorphine and naloxone administered to the patient.

Embodiment 12: A method of treating opioid dependence in a patient with depression, the method comprising: administering a sublingual dose of buprenorphine and naloxone to the patient effective to manage the patient's withdrawal symptoms and cravings for an opioid; and in conjunction with the administration of the sublingual dose of buprenorphine and naloxone, engaging in a self-directed digital, interactive cognitive behavioral therapy program that treats depression, wherein the depression is treated, and wherein at least one of the patient's use of opioids decreases or the patient's use of opioids occurs at a higher pain intensity level compared to the patient's use of opioids prior to the patient's engagement with the self-directed digital, interactive cognitive behavior therapy program.

Embodiment 13: A method of treating opioid dependence in a patient, the method comprising: administering a sublingual dose of buprenorphine and naloxone to the patient effective to manage the patient's withdrawal symptoms and cravings for an opioid; and in conjunction with the administration of the sublingual dose of buprenorphine and naloxone, engaging in a self-directed digital, interactive cognitive behavioral therapy program that treats depression, wherein the risk of depression in the patient is decreased, and wherein at least one of the patient's use of opioids decreases or the patient's use of opioids occurs at a higher pain intensity level compared to the patient's use of opioids prior to the patient's engagement with the self-directed digital, interactive cognitive behavior therapy program.

Embodiment 14: A method of reducing the risk of opioid dependence relapse in a patient with depression and a history of opioid dependence, the method comprising: administering a sublingual dose of buprenorphine and naloxone to the patient effective to manage the patient's withdrawal symptoms and cravings for an opioid; and in conjunction with the administration of the sublingual dose of buprenorphine and naloxone, engaging in a self-directed digital, interactive cognitive behavioral therapy program that treats depression, wherein the depression is treated, thereby reducing the risk of opioid dependence relapse in the patient.

Embodiment 15: A method of treating opioid dependence in a patient with depression, the method comprising: administering a sublingual dose of buprenorphine and naloxone to the patient in a treatment regimen effective to manage the patient's withdrawal symptoms and cravings; and in conjunction with the administration of the sublingual dose of buprenorphine and naloxone, engaging in a self-directed digital, interactive cognitive behavioral therapy program that treats the depression, wherein the depression is treated, thereby increasing adherence by the patient to the treatment regimen.

Embodiment 16: A method of treating opioid dependence in a patient with depression, the method comprising: administering a sublingual dose of buprenorphine and naloxone to the patient in a treatment regimen effective to manage the patient's withdrawal symptoms and cravings for an opioid; and in conjunction with the administration of the sublingual dose of buprenorphine and naloxone, engaging in a self-directed digital, interactive cognitive behavioral therapy program that treats depression, wherein the depression is treated, thereby causing the patient to decrease concomitant use of a benzodiazepine and decreasing a risk of an adverse reaction or drug interaction between the benzodiazepine and the sublingual dose of buprenorphine and naloxone administered to the patient, thereby improving a safety profile of the sublingual dose of buprenorphine and naloxone administered to the patient.

Embodiment 17: A method of treating opioid dependence in a patient with depression, the method comprising: administering a sublingual dose of buprenorphine and naloxone to the patient in a treatment regimen effective to manage the patient's withdrawal symptoms and cravings; and in conjunction with the administration of the sublingual dose of buprenorphine and naloxone, engaging in a self-directed digital, interactive cognitive behavioral therapy program that treats the depression, wherein the depression is treated, thereby increasing adherence by the patient to the treatment regimen and causing the patient to decrease concomitant use of a benzodiazepine, thereby decreasing a risk of an adverse reaction or drug interaction between the benzodiazepine and the sublingual dose of buprenorphine and naloxone administered to the patient, thereby improving a safety profile of the sublingual dose of buprenorphine and naloxone administered to the patient.

Embodiment 18: The method of any one of Embodiments 1-17, wherein the patient is suffering from chronic depression.

Embodiment 19: The method of any one of Embodiments 1-17, wherein the patient is suffering from recurrent depression.

Embodiment 20: The method of any one of Embodiments 1-17, wherein the patient is suffering from mild-to-moderate depression.

Embodiment 21: The method of any one of Embodiments 1-20, wherein OAT comprises administering ZUBSOLV®.

Embodiment 22: The method of any one of Embodiments 1-21, wherein the program is accessed remotely.

Embodiment 23: The method of any one of Embodiments 1-22, wherein the program is accessible via computer or device.

Embodiment 24: The method of any one of Embodiments 1-23, wherein the program is a fully automated digital therapy.

Embodiment 25: The method of any one of Embodiments 1-24, wherein the program is web-based.

Embodiment 26: The method of any one of Embodiments 1-25, wherein the program is cloud-based.

Embodiment 27: The method of any one of Embodiments 1-26, wherein a physician is involved in the patient use of the program.

Embodiment 28: The method of any one of Embodiments 1-27, wherein a physician is not involved in the patient use of the program.

Embodiment 29: The method of any one of Embodiments 1-28, wherein the program is tailored to individual patients.

Embodiment 30: The method of any one of Embodiments 1-29, wherein the program is a 10-week (or 12-week) course of modules.

Embodiment 31: The method of Embodiment 30, wherein there are ten modules covering the following topics:
A. Psychoeducation
B. behavioral activation
C. cognitive modification
D. mindfulness and acceptance E. interpersonal skills F. relaxation, physical exercise and lifestyle modification G. problem solving H. expressive writing and forgiveness or childhood experiences I. positive psychological interventions J. dream work and emotion-focused interventions.

Embodiment 32: The method of Embodiment 31, wherein the ten modules are taken in the order A to J.

Embodiment 33: The method of any one of Embodiments 1-32, wherein the patient has access to the program for use at any time of day or night.

Embodiment 34: The method of any one of Embodiments 1-33, wherein the program content is adjusted based on input from the patient.

Embodiment 35: The method of Embodiment 34, wherein the program content is adjusted using artificial intelligence to analyze input from the patient.

Embodiment 36: The method of any one of Embodiments 1-35, wherein the program comprises a mobile medical application.

Embodiment 37: The method of Embodiment 36, wherein the mobile medical application is accessible from a mobile device, such as a laptop computer, a tablet or a smartphone.

Embodiment 38: The method of Embodiment 36, wherein the mobile medical application is accessible from a wearable device.

Embodiment 39: The method of Embodiment 38, wherein the wearable device is used to drive further content for, and patient interaction with, the program.

Embodiment 40: The method of any one of Embodiments 36-39, wherein the mobile medical application is DEPREXIS®.

Embodiment 41: The method of any one of Embodiments 1-40, wherein the patient is at least 18 years of age.

Embodiment 42: The method of any one of Embodiments 1-41, wherein the patient has multiple sclerosis.

Embodiment 43: The method of any one of Embodiments 1-41, wherein the patient has epilepsy.

Embodiment 44: The method of any one of Embodiments 1-43, wherein the patient achieves an improvement of at least 1, 2, 3, 4, 5 or 6 Beck depression inventory points.

Embodiment 45: The method of Embodiment 44, wherein the improvement is substantially maintained for at least 3, 4, 5 or 6 months.

Embodiment 46: The method of Embodiment 44, wherein an improvement is obtained when the patient completes less than 10, 9, 8, 7, 6, 5 or 4 of the program modules.

Embodiment 47: The method of Embodiment 44, wherein an improvement is obtained when the patient completes the first 1, 2, 3 or 4 program modules.

Embodiment 48: The method of any one of Embodiments 1-47, wherein a therapist guides the patient through the program.

Embodiment 49: The method of Embodiment 48, wherein a manual is provided to assist the therapist in guiding the patient through the program.

Embodiment 50: The method of any one of Embodiments 1-49, wherein the self-directed digital, interactive cognitive behavioral therapy program comprises a web-based software program.

Embodiment 51: The method of any one of Embodiments 1-50, wherein engaging in the self-directed digital, interactive cognitive behavioral therapy program comprises entering a unique user ID.

Embodiment 52: The method of any one of Embodiments 1-51, wherein the self-directed digital, interactive cognitive behavioral therapy program comprises a plurality of modules and each of the plurality of modules utilizes a different psychotherapeutic approach.

Embodiment 53: The method of Embodiment 52, wherein the plurality of modules comprises at least one of a psychoeducation module, a behavioral activation module, a cognitive modification module, a mindfulness and acceptance module, an interpersonal skills module, a relaxation module, a physical exercise and lifestyle modification module, a problem solving module, an expressive writing and forgiveness or childhood experiences module, a positive psychological interventions module, or a dream work and emotion-focused interventions module.

Embodiment 54: The method of any one of Embodiments 1-53, wherein the patient engages in the self-directed digital, interactive cognitive behavioral therapy program for about eight to about twelve weeks.

Embodiment 55: The method of any one of Embodiments 1-54, wherein the patient engages in the self-directed digital, interactive cognitive behavioral therapy program once or twice per week.

Embodiment 56: The method of Embodiment 55, wherein patient engages in the self-directed digital, interactive cognitive behavioral therapy program for at least 30 minutes per session.

Embodiment 57: The method of any one of Embodiments 1-56, wherein engaging in the self-directed digital, interactive cognitive behavioral therapy program results in at least a 50% improvement in symptoms associated with the depression.

Embodiment 58: The method of any one of Embodiments 1-57, wherein the sublingual dose comprises about 11.4 mg of buprenorphine and about 2.9 mg of naloxone once daily.

Embodiment 59: The method of any one of Embodiments 1-58, wherein the sublingual dose comprises from about 0.7 mg to about 11.4 mg of buprenorphine and from about 0.18 mg to about 2.9 mg of naloxone once daily.

Embodiment 60: The method of any one of Embodiments 1-59, wherein treating the opioid dependence comprises at least one of a decrease in an amount of opioid use by the patient, a decrease in a frequency of the opioid use by the patient, an increase in a number of number of days between instances of the opioid use by the patient, or an increase pain tolerance exhibited by the patient before the opioid use.

Embodiment 61: The method of any one of Embodiments 1-60, wherein engaging with the self-directed digital, interactive cognitive behavioral therapy program occurs at least one of prior to, contemporaneously with, or subsequent to the administration of the sublingual dose of buprenorphine and naloxone.

Embodiment 62: The method of any one of Embodiments 1-61, wherein engaging with the self-directed digital, interactive cognitive behavioral therapy program at least partially temporally overlaps with the administration of the sublingual dose of buprenorphine and naloxone.

EXAMPLES

Example 1: Treatment of Depression Using DEPREXIS®

Method: A controlled trial was conducted in a US population of 376 patients with at least moderate depression (QIDS-SR score ≥10 out of a possible 27); baseline scores were in the high moderate range (mean score 15.19). The Quick Inventory of Depression Symptoms (QIDS-SR) is a 16-item self-report questionnaire that assesses the nine diagnostic symptom domains used to characterize a major depressive episode. Secondary outcomes included the Hamilton Rating Scale for Depression (HRSD), aspects of depression and anxiety via the Inventory of Depression and Anxiety Symptoms (IDAS): Ill Temper, Well-Being, Social Anxiety, Traumatic Intrusions, and Panic. To be included in the study, the subject was: (a) aged between 18 and 55; (b) fluent in English; (c) had reliable access to the Internet (i.e., dialup or broadband access); (d) willing to provide saliva for DNA research; (e) exhibited moderate levels of depression; (f) treatment stable (no changes in psychotropic medication or psychosocial treatment in the 30 days before study entry); and (g) living in the United States of America. Patients were randomized 3:1 (285:91) to either DEPREXIS® or the control arm for 8 weeks. The control group received access to DEPREXIS® after the week 8 assessments. The patient population was principally female in their early thirties, single and non-Hispanic white. Approximately 40% of the population were currently receiving antidepressants and more than two-thirds had received psychological treatment at some point There was minimal contact between the patient and study personnel, except for a pre-randomization interview to obtain a suicide history and an assessment for bipolar disorder.

Results: The intention-to-treat (ITT) analysis revealed that DEPREXIS® treatment was associated with greater reduction in self-reported symptoms of depression (effect size d 0.80) and 12 times greater likelihood of experiencing at least 50% symptom improvement compared with control. Treatment effects for symptoms of social anxiety, panic, & traumatic intrusions were relatively small.

Conclusion: DEPREXIS® a minimally supported and easily accessible internet intervention, was found to be effective in persons with moderate depression when compared with "care as usual" for adults with depression. (C. Beevers, J Consult Clin Psychol, vol. 85, pp. 1-14, 2017).

Example 2: Treatment of Depression Using DEPREXIS® During Opioid Agonist Therapy Patients are initially inducted using buprenorphine sublingual tablets (particularly when dependent on methadone or long-acting opioid products) or ZUBSOLV®. ZUBSOLV® sublingual tablets are then administered sublingually as a single daily dose.

At treatment initiation, the first dose of ZUBSOLV® is administered when objective signs of moderate opioid withdrawal appear, not less than six hours after the patient last used opioids, to avoid precipitating an opioid withdrawal syndrome. An adequate treatment dose, titrated to clinical effectiveness, is administered as rapidly as possible. On Day 1, an induction dosage of up to 5.7 mg/1.4 mg ZUBSOLV® is administered, starting with an initial dose of 1.4 mg/0.36 mg ZUBSOLV®. The remainder of the Day 1 dose of up to 4.2 mg/1.08 mg is divided into doses of 1 to 2 tablets of 1.4 mg/0.36 mg at 1.5 to 2 hour intervals. Some patients (e.g., those with recent exposure to buprenorphine) can tolerate up to 3×1.4 mg/0.36 mg ZUBSOLV® as a single, second dose. On Day 2, a single daily dose of up to 11.4 mg/2.9 mg ZUBSOLV® is administered.

The dosage of ZUBSOLV® from Day 3 onwards is progressively adjusted in increments/decrements of 2.9 mg/0.71 mg or lower of buprenorphine/naloxone to a level that holds the patient in treatment and suppresses opioid withdrawal signs and symptoms. After treatment induction and stabilization, the maintenance dose of ZUBSOLV is generally in the range of 2.9 mg/0.71 mg buprenorphine/naloxone to 17.2 mg/4.2 mg buprenorphine/naloxone per day depending on the individual patient and clinical response. The target dosage of ZUBSOLV® during maintenance is 11.4 mg/2.9 mg as a single daily dose.

ZUBSOLV® sublingual tablet is placed under the tongue until dissolved. The dissolve time for ZUBSOLV® varies between individuals, and the median dissolve time observed is 5 minutes. When more than one sublingual tablet is administered, all tablets are deposited in different places under the tongue at the same time. Patients keep the tablets under the tongue until dissolved as swallowing the tablets reduces the bioavailability of the drug. Patients are advised not to eat or drink anything until the tablet is completely dissolved.

Treatment of ZUBSOLV® is initiated with supervised administration, progressing to unsupervised administration as the patient's clinical stability permits. When determining the prescription quantity for unsupervised administration, consideration is given to the patient's level of stability, the security of his or her home situation, and other factors likely to affect the ability to manage supplies of take-home medication. Patients are seen at reasonable intervals (e.g., at least weekly during the first month of treatment) based upon the individual circumstances of the patient. Once a stable dosage of ZUBSOLV® is achieved and patient assessment (e.g., urine drug screening) does not indicate illicit drug use, less frequent follow-up visits are appropriate. A once-monthly visit schedule is reasonable for patients on a stable dosage of medication who are making progress toward their treatment objectives. Continuation or modification of pharmacotherapy is based on the physician's evaluation of treatment outcomes and objectives such as:

1. Absence of medication toxicity
2. Absence of medical or behavioral adverse effects
3. Responsible handling of medications by the patient
4. Patient's compliance with all elements of the treatment plan (including recovery-oriented activities, psychotherapy, and/or other psychosocial modalities)
5. Abstinence from illicit drug use (including problematic alcohol and/or benzodiazepine use)

If treatment goals are not being achieved, the physician will reevaluate the appropriateness of continuing the current treatment.

Further details of the maintenance treatment of opioid dependence using ZUBSOLV® are given in the ZUBSOLV® product label, available at: https://www.accessdata.fda.gov/scripts/cder/daf/, and incorporated by reference herein in its entirety.

During maintenance treatment of opioid dependence using ZUBSOLV®, the patient also starts a 12-week DEPREXIS® program. Patient data is collected throughout the duration of the DEPREXIS® program, including patient reported outcomes for both management of opioid dependence and depression.

All papers cited herein and relevant drug product labels are incorporated by reference herein in their entirety.

The invention claimed is:

1. A method of treating opioid dependence in a patient with depression, the method comprising:
   administering a sublingual dose of buprenorphine and naloxone to the patient in a treatment regimen effective to manage the patient's withdrawal symptoms and cravings; and
   in conjunction with the administration of the sublingual dose of buprenorphine and naloxone, engaging in a self-directed digital, interactive cognitive behavioral therapy program provided via a software application that treats the depression,
   wherein the software application comprises a plurality of modules providing therapeutic content implementing a plurality of psychotherapeutic approaches,
   wherein the software application receives feedback from the patient and, based on the feedback, adjusts at least one of (i) an order in which the plurality of modules are presented to the patient or (ii) the digital therapeutic content provided by the plurality of modules,
   wherein the depression is treated, thereby increasing adherence by the patient to the treatment regimen.

2. The method of claim 1, wherein the self-directed digital, interactive cognitive behavioral therapy program comprises a web-based software program.

3. The method of claim 1, wherein the feedback comprises reading and answering material provided via the plurality of modules that is configured to simulate a conversational flow.

4. The method of claim 1, wherein the plurality of modules comprises at least one of a psychoeducation module, a behavioral activation module, a cognitive modification module, a mindfulness and acceptance module, an interpersonal skills module, a relaxation module, a physical exercise and lifestyle modification module, a problem solving module, an expressive writing and forgiveness or childhood experiences module, a positive psychological interventions module, or a dream work and emotion-focused interventions module.

5. The method of claim 1, wherein the sublingual dose comprises from about 0.7 mg to about 11.4 mg of buprenorphine and from about 0.18 mg to about 2.9 mg of naloxone once daily.

6. The method of claim 1, wherein the depression is treated by decreasing at least one of anxiety, panic, traumatic intrusions, or suicidal intent exhibited by the patient.

7. The method of claim 1, wherein engaging with the self-directed digital, interactive cognitive behavioral therapy program at least partially temporally overlaps with the administration of the sublingual dose of buprenorphine and naloxone.

8. A method of treating opioid dependence in a patient with depression, the method comprising:
   administering a sublingual dose of buprenorphine and naloxone to the patient in a treatment regimen effective to manage the patient's withdrawal symptoms and cravings for an opioid; and
   in conjunction with the administration of the sublingual dose of buprenorphine and naloxone, engaging in a self-directed digital, interactive cognitive behavioral therapy program provided via a software application that treats the depression,
   wherein the software application comprises a plurality of modules providing therapeutic content implementing a plurality of psychotherapeutic approaches,
   wherein the software application receives feedback from the patient and, based on the feedback, adjusts at least one of (i) an order in which the plurality of modules are presented to the patient or (ii) the digital therapeutic content provided by the plurality of modules,
   wherein the depression is treated, thereby causing the patient to decrease concomitant use of a benzodiazepine and decreasing a risk of an adverse reaction or drug interaction between the benzodiazepine and the sublingual dose of buprenorphine and naloxone administered to the patient, thereby improving a safety profile of the sublingual dose of buprenorphine and naloxone administered to the patient.

9. The method of claim 8, wherein the self-directed digital, interactive cognitive behavioral therapy program comprises a web-based software program.

10. The method of claim 8, wherein the feedback comprises reading and answering material provided via the plurality of modules that is configured to simulate a conversational flow.

11. The method of claim 8, wherein the plurality of modules comprises at least one of a psychoeducation module, a behavioral activation module, a cognitive modification module, a mindfulness and acceptance module, an interpersonal skills module, a relaxation module, a physical exercise and lifestyle modification module, a problem solving module, an expressive writing and forgiveness or childhood experiences module, a positive psychological interventions module, or a dream work and emotion-focused interventions module.

12. The method of claim 8, wherein the sublingual dose comprises from about 0.7 mg to about 11.4 mg of buprenorphine and from about 0.18 mg to about 2.9 mg of naloxone once daily.

13. The method of claim 8, wherein the depression is treated by decreasing at least one of anxiety, panic, traumatic intrusions, or suicidal intent exhibited by the patient.

14. The method of claim 8, wherein engaging with the self-directed digital, interactive cognitive behavioral therapy program at least partially temporally overlaps with the administration of the sublingual dose of buprenorphine and naloxone.

15. The method of claim 1, wherein the software application is configured to at least one of:
   provide a healthcare provider status information associated with use of the software application by the patient, or
   allow the patient to communicate with the healthcare provider.

16. The method of claim 8, wherein the software application is configured to at least one of:
   provide a healthcare provider status information associated with use of the software application by the patient, or
   allow the patient to communicate with the healthcare provider.

17. A method of treating opioid dependence in a patient with depression, the method comprising:
   administering a sublingual dose of buprenorphine and naloxone to the patient in a treatment regimen effective to manage the patient's withdrawal symptoms and cravings; and
   in conjunction with the administration of the sublingual dose of buprenorphine and naloxone, engaging in an interactive online-based program that provides a fully automated digital cognitive behavioral therapy program for treating the depression, wherein the digital cognitive behavioral therapy program is configured to be adjusted based on input received from the patient, wherein the depression is treated, thereby increasing adherence by the patient to the treatment regimen.

18. The method of claim 17, wherein the input comprises reading and answering material provided via the plurality of modules that is configured to simulate a conversational flow.

19. The method of claim 17, wherein the digital cognitive behavioral therapy program comprises a plurality of modules.

20. The method of claim 19, wherein the plurality of modules comprises at least one of a psychoeducation module, a behavioral activation module, a cognitive modification module, a mindfulness and acceptance module, an interpersonal skills module, a relaxation module, a physical exercise and lifestyle modification module, a problem solving module, an expressive writing and forgiveness or childhood experiences module, a positive psychological interventions module, or a dream work and emotion-focused interventions module.

21. The method of claim 17, wherein the depression is treated by decreasing at least one of anxiety, panic, traumatic intrusions, or suicidal intent exhibited by the patient.

22. The method of claim 17, wherein the digital cognitive behavioral therapy program is configured to at least one of:
provide a healthcare provider status information associated with use of the software application by the patient, or
allow the patient to communicate with the healthcare provider.

* * * * *